United States Patent
Drossler

[11] Patent Number: 5,577,285
[45] Date of Patent: Nov. 26, 1996

[54] ELECTRIC TOOTHBRUSH WITH ROTARY BRISTLE SUPPORTING STRUCTURE

[75] Inventor: Michael Drössler, Oberursel, Germany

[73] Assignee: Braun Aktiengesellschaft, Kronberg, Germany

[21] Appl. No.: 256,520

[22] PCT Filed: Oct. 29, 1993

[86] PCT No.: PCT/EP93/03024

§ 371 Date: Jul. 15, 1994

§ 102(e) Date: Jul. 15, 1994

[87] PCT Pub. No.: WO94/12121

PCT Pub. Date: Jun. 9, 1994

[30] Foreign Application Priority Data

Nov. 21, 1992 [DE] Germany ............ 42 39 251.9

[51] Int. Cl.$^6$ ........................................ A61C 17/34
[52] U.S. Cl. ........................................ 15/22.1; 15/28
[58] Field of Search ........................ 15/22.1, 22.4, 15/28, 29

[56] References Cited

U.S. PATENT DOCUMENTS

| | | | |
|---|---|---|---|
| 1,255,028 | 1/1918 | Leonard et al. | 15/22.1 |
| 4,281,987 | 8/1981 | Kleesattel | 15/22.1 |
| 4,432,729 | 2/1984 | Fattaleh | 15/22.1 |
| 4,479,516 | 10/1984 | Hunter | 15/28 |
| 4,827,552 | 5/1989 | Bojar et al. | 15/28 |

FOREIGN PATENT DOCUMENTS

| | | |
|---|---|---|
| 1766651 | 8/1971 | Germany . |
| 3233266 | 10/1983 | Germany . |
| 3505897 | 8/1986 | Germany . |
| 3937850 | 5/1991 | Germany . |
| 9304184 U | 7/1993 | Germany . |
| 1208149 | 10/1970 | United Kingdom . |
| 1583558 | 1/1981 | United Kingdom . |

*Primary Examiner*—Mark Spisich
*Attorney, Agent, or Firm*—Fish & Richardson, P.C.

[57] ABSTRACT

A brush section (24) for an electric toothbrush in which a rotary shaft (34) is received which is adapted to perform an alternating or a rotary motion. Mounted on the brush section (24) is a rotary bristle supporting structure (38) having its axis of rotation (54) disposed at about right angles to the axis of rotation (52) of the shaft (34). The shaft (34) receives movably therein a rod (102) disposed approximately parallel and eccentrically. In an annular shoulder (61) of the bristle supporting structure (38), a pin (112) is held, extending approximately parallel and eccentrically to the axis of rotation (54). The pin (112) is passed through an eyelet (103) provided at the free end of the rod (102) and is movable therein. When the shaft (34) is caused to perform a rotary or alternating motion, this motion is transmitted to the bristle supporting structure (38) through the rod (102), the eyelet (103), and the pin (112). The bristle supporting structure (38) will invariably perform a rotary alternating motion, irrespective of whether the shaft (34) is driven to perform an alternating or a rotary motion.

39 Claims, 8 Drawing Sheets

ELECTRIC TOOTHBRUSH WITH ROTARY BRISTLE SUPPORTING STRUCTURE

This invention relates to an electric toothbrush with a brush section in which a rotary shaft is received and on which a rotary bristle supporting structure is mounted, with the axis of rotation of the bristle supporting structure being angularly arranged, in particular at about right angles, to the axis of rotation of the shaft, and with means being provided enabling the shaft to drive the bristle supporting structure in alternate directions.

A toothbrush of this type is known from German published patent application DE 39 37 850 A1. In this specification, the bristle supporting structure is driven by means of a bevel gear train. While this structure has proven to be very successful in practice, it requires the shaft of the electric toothbrush to be driven in alternate directions.

Further, from German published patent application DE 17 66 651 A1 a device for cleaning and polishing teeth is known, in which a bolt projecting eccentrically from a shaft engages in an outer annular groove of a displaceable cylinder having further a conical center bore adapted to receive an implement for cleaning the teeth. Rotation of the shaft causes, through the eccentric bolt, an up-and-down motion of the cylinder and consequently also of the cleaning implement. Due to the outer annular groove, the cleaning implement is at the same time rotatable about its longitudinal axis, so that the implement adjusts itself to its angular position as it enters, for example, an interproximal space. However, the cleaning implement is not driven so as to perform an alternating motion about its longitudinal axis.

Still further, from German published patent application DE 32 33 266 A1 a device for the prophylactic treatment of caries by giving the enamel of teeth a mechanical massage is known, in which an eccentric pin projects from a disc secured to a shaft. The shank end of a massage cup is inserted in a sleeve provided with a longitudinal groove. This longitudinal groove is operatively associated with the eccentric pin such that, when the pin engages within the longitudinal groove, it causes the longitudinal groove to follow its movement as the shaft rotates, thus causing also the sleeve to perform a rotary motion. However, when the pin does not engage the longitudinal groove, as illustrated, for example, in FIG. 2a of the published patent application, this has the result that the shaft is not in coupling engagement with the sleeve. When the shaft is then caused to rotate, it may happen that the pin does not pick up the sleeve because of the lack of coupling engagement. This risk exists particularly when the shaft is driven in alternate directions, because in this event the longitudinal groove of the sleeve is decoupled from the pin precisely at the instant when the rotary motion reverses direction. At all events, this device allows only such an alternating motion of the massage head in which the angle of rotation is greatly limited. Also, the shaft cannot be driven to rotate because then the device would not be functional. Thus, the known device is of limited effect in addition to being complicated in structure.

In GB-PS 1 208 149 a cleaning apparatus is described having two concentric cleaning rings driven in relatively opposite directions by means of bevel gars.

It is an object of the present invention to provide an electric toothbrush which, while affording a straightforward construction, allows the bristle supporting structure to be driven in alternate directions over a large angle of rotation and, where applicable, also allows its shaft to perform rotary or alternating motions.

This object is essentially solved in that the shaft is provided with a driving means disposed eccentrically to its axis of rotation, that the bristle supporting structure is provided with a driven means disposed eccentrically to its axis of rotation, and that the driving means and the driven means are coupled to each other.

This arrangement ensures that the bristle supporting structure is caused to rotate in alternate directions irrespective of whether the shaft performs a rotary motion or a rotary motion reversing direction in alternating sequence. In either event, the eccentric driving means and the eccentric driven means ensure a reliable transmission of the rotary motions also over large angles of rotation. By coupling the driving means to the driven means, it is ensured that the operative association between these two components is maintained at all events. To provide for an alternating motion of the bristle supporting structure, only the eccentric driving means and the eccentric driven means are accordingly required. Further components, in particular gear components, can be omitted. The overall structure of the electric toothbrush is thereby simplified.

In an advantageous embodiment, the driving means is a rod received in a bore arranged approximately parallel to the axis of rotation of the shaft. Thus, the driving means is comprised of only a single component suitably made of metal, that is, the rod disposed parallel to the axis of rotation.

Further, the driven means may be a pin received in a bore arranged approximately parallel to the axis of rotation of the bristle supporting structure. Also in this arrangement, only a single component is required for the driven means, that is, the pin disposed parallel to the axis of rotation of the bristle supporting structure. Conveniently, this pin is equally made of metal.

The rod and the pin may be fixedly connected with each other or alternatively, they may be an integrally formed structure. Advantageously, the mounts receiving the rod and the pin are configured such that both the rod and the pin are in a position to rotate within their respective mounts as well as to move in their respective axial directions.

In another advantageous embodiment, the rod has at its free end an eyelet through which the pin is passed. In this embodiment, the bore of the rod is advantageously configured such as to allow the rod to rotate as well as to move in an axial direction. Further, the eyelet is rotatable about the pin and movable in the latter's axial direction.

In either embodiment providing for coupling engagement between the rod and the pin, a reliable connection between these components is ensured. In normal operation, it is not possible to uncouple the rod from the pin.

In particular the embodiment in which the rod is provided with an eyelet affords the added advantage of a straightforward and speedy assembly.

Moreover, use of the eccentric rod and the eccentric pin has the advantage that the angular range of the alternating rotary motion of the bristle supporting structure can be readily adjusted by varying the degree of eccentricity of the rod or pin. Accordingly, it is possible to increase or decrease the angular range of the alternating rotary motion of the bristle supporting structure in dependence upon the relative distance of, for example, the rod and the axis of rotation of the shaft.

In another advantageous embodiment, the bristle supporting structure is pivotally mounted in the brush section. To this end, the bristle supporting structure is provided with an axle received in a ball bearing by means of a bearing ball, for example. Thus, the bristle supporting structure, while continuing to be rotatable about its own axis of rotation, is also pivotal about the ball bearing.

If in this configuration the driving means is configured as a rod and the driven means as a pin, and if, in a modification of the previous embodiments, the bore receiving the rod is configured such as to allow rotation of the rod, yet inhibiting its movement in the axial direction, this has the result of causing the bristle supporting structure to perform an alternating rotary and wobbling motion. This advantageous embodiment enhances the cleaning effect of the electric toothbrush.

In still another advantageous embodiment, the bristle supporting structure includes an outer and an inner bristle ring which are both rotary about the axis of rotation of the bristle supporting structure. The outer and the inner bristle ring are operatively associated with a respective driven means each being again coupled to a respective driving means. Conveniently, the driving means are eccentrically disposed on relatively opposite sides of the axis of rotation of the shaft. In consequence, the outer and the inner bristle ring perform an alternating motion in opposite directions of rotation, whereby the cleaning effect of the toothbrush is improved.

In a particular feature, the bristle supporting structure includes an eccentric bore opening at least towards the underside of the bristle supporting structure, with the driven means and the driving means being configured as a transmission element integrally made of one piece. This ensures particularly great ease of assembly of the transmission element in the toothbrush.

Advantageously, in a mid-section of the bristle supporting structure the bore has an aperture towards the side wall of the bristle supporting structure. This aperture allows passage of the rod of the transmission element, enabling it to be readily introduced into the mount provided in the shaft.

The transmission element is advantageously of a T-shaped configuration, the diameter of the rod being preferably smaller than the diameter of the pin. This provides the possibility of having both end portions of the pin carried in the bristle supporting structure while yet affording ease of assembly of the transmission element on the bristle supporting structure. It will be understood, of course, that the transmission element may also be configured in L-shape or any other suitable shape.

In a further embodiment of this invention, a lower portion of the bore of the bristle supporting structure includes an opening which extends radially to the side wall in particular in the manner of a longitudinal slot and includes preferably a narrowing formed by extensions. This embodiment affords the advantage of great ease of assembly, because the pin of the particularly T-shaped transmission element is simply inserted in the bore from the underside of the bristle supporting structure, while the rod of the transmission element is received by the longitudinally slotted opening as this assembly operation is being performed. On completion of assembly of the transmission element, its rod will extend through the aperture provided in the mid-section of the bristle supporting structure up to the shaft of the brush section. The narrowing in the longitudinal slot formed by the extensions serves to support on the bristle supporting structure also that portion of the pin that points to the underside of the bristle supporting structure. Because the diameter of the rod is preferably smaller than the diameter of the pin, the rod can be passed through the narrowing as it is mounted on the bristle supporting structure, the extensions then forming a kind of abutment for the pin on completion of the assembly operation. The other portion of the pin is carried in the bore in the bristle supporting structure.

In another, greatly advantageous embodiment of this invention, a lower portion of the bore of the bristle supporting structure provides an essentially chord-like notch open towards the underside, which extends away from the bore to a portion of the side wall and is in communication with a further notch provided in the side wall. In this embodiment, the transmission element is equally assembled so that its pin is introduced into the bore from below, this requiring the transmission element to be positioned such that the rod is received in the notch open towards the underside. The transmission element is displaced axially to the upper side of the bristle supporting structure until the rod engages within the notch provided in the side wall. This then enables the rod to be swung from this position radially outwardly about the pin to occupy its final, assembled position. This further embodiment has the great advantage that the pin is fixedly located on the bristle supporting structure at either end portion thereof, in addition to being securely captured in the bore. Also this way of assembling the transmission element on the bristle supporting structure is extremely easy and can be performed with suitable machinery.

In particular, not all embodiments require the axis of rotation of the bristle supporting structure to be at about right angles to the axis of rotation of the shaft and/or the driven means configured as a pin to be approximately parallel to the axis of rotation of the bristle supporting structure. By arranging these components at different angles, beneficial effects are obtainable on the alternating motion of the bristle supporting structure in respect of angle of rotation, circular acceleration, and further parameters.

Further features, advantages and application possibilities of the present invention will become apparent from the subsequent description of embodiments illustrated in more detail in the accompanying drawings. It will be understood that all features described and/or represented by illustration, whether taken alone or in any desired combination, constitute the subject-matter of the present invention, irrespective of their summarization in the claims and their back-references.

The description that follows is based on applicant's German published patent application DE 39 37 850 A1 initially referred to the disclosure content of which is included in the present description by express reference thereto. In particular, reference is made to the general description of the electric toothbrush in connection with FIG. 1 of German published patent application DE 39 37 850 A1.

Figure 1:
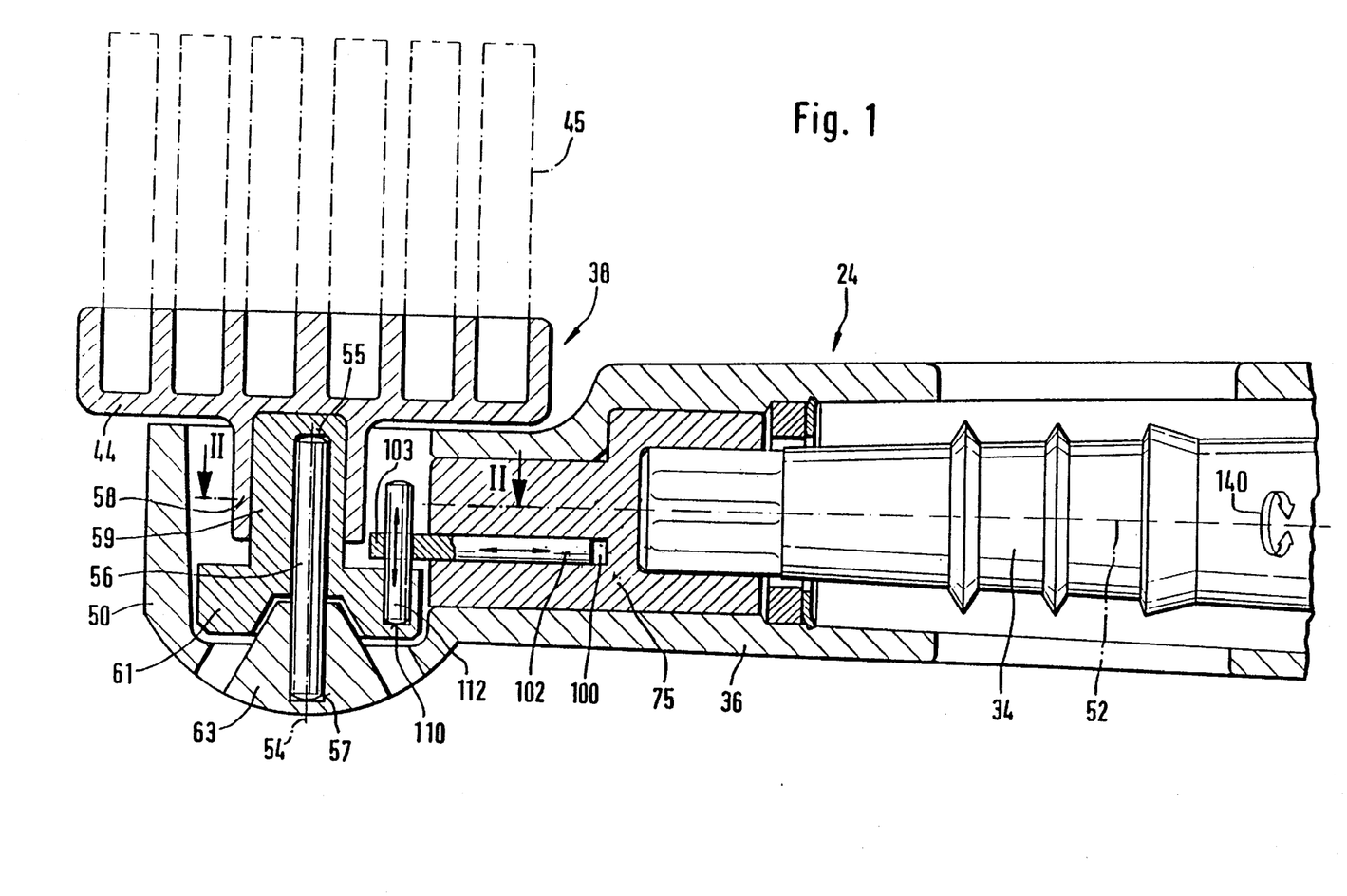
FIG. 1 is a schematic sectional view of a first embodiment of the brush section of an electric toothbrush constructed in accordance with the present invention, in which the shaft is driven to perform an alternating motion.
Figure 10:
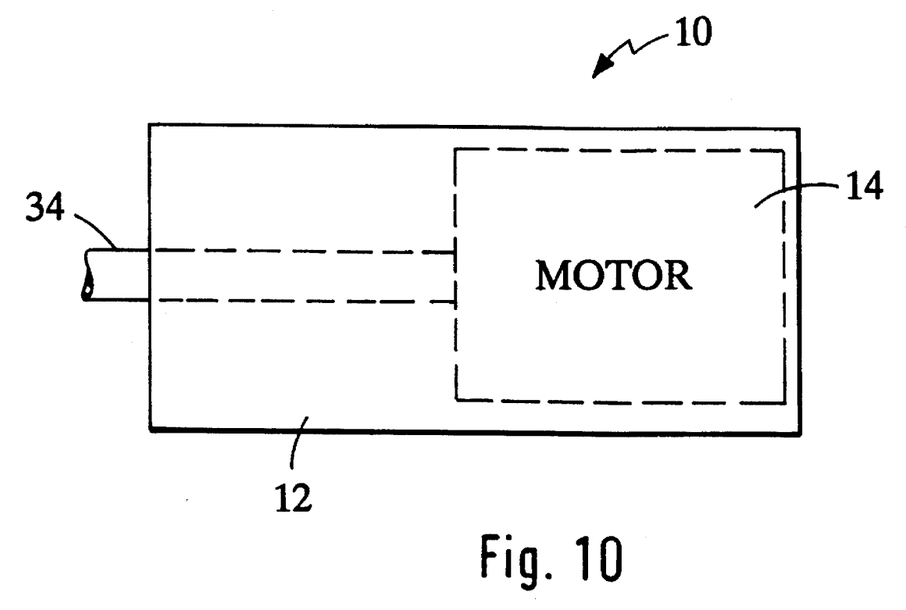
FIG. 10 is a diagrammatic view of the handle section of the toothbrush.

In a first embodiment, FIG. 1 shows a brush section 24 which is adapted to be coupled to a handle section 12 of an electric toothbrush 10 (see FIG. 10). The brush section 24 is comprised of a hollow mounting tube 36 receiving a shaft 34 with a shaft member 75 seated thereon. The shaft 34 is coupled to an electric motor accommodated in the handle section of the toothbrush, the motor 14 causing the shaft 34 to rotate in alternate directions. This is shown in FIG. 1 by the arrow 140.

At its end remote from the handle section of the toothbrush, the mounting tube 36 merges into an upwardly open, cup-shaped socket 50. The socket 50 accommodates a bristle supporting structure 38, a mounting plate 44 thereof carrying bristles 45 and covering the opening of the socket 50. At the side of the socket 50 remote from the mounting plate 44, an elevation 63 is provided in which a blind-end bore 57 is formed. The blind-end bore 57 receives an axle 56 on which the bristle supporting structure 38 is rotatably mounted.

Seated down on the axle 56 by means of a blind-end bore 55 is a trunnion 59 widening to form an annular shoulder 61 at its end facing the elevation 63. A bushing section 58 formed with the mounting plate 44 is seated on the trunnion 59 in positive engagement therewith.

The complete bristle supporting structure 38 comprising the mounting plate 44 with its bristles 45 as well as the trunnion 59 with its annular shoulder 61 is rotatably mounted about the axis of rotation 54 formed by the axle 56. Equally, the shaft 34 with its shaft member 75 is mounted so as to be rotatable about the axis of rotation 52 formed by the shaft 34, said axis of rotation representing at the same time the longitudinal center line of the mounting tube 36 and thus of the brush section 24. The axis of rotation 54 of the bristle supporting structure 38 extends angularly to the axis of rotation 52 of the shaft 34, the angle being of the order of 90°, approximately.

An eccentric bore 100 is formed in the shaft member 75 at its end facing the socket 50, said bore extending approximately parallel to the axis of rotation 52 of the shaft 34, yet at a relative distance to said axis of rotation 52. The bore 100 receives a rod 102 having an eyelet 103 at its free end projecting from the shaft member 75. The diameter of the bore 100 is slightly larger than the diameter of the rod 102. In this manner, the rod 102 is allowed to rotate inside the bore 100 about its own axis, as well as to move back and forth in an axial direction.

In the area of the annular shoulder 61 close to the shaft member 75, an eccentric bore 110 is formed extending parallel to the axis of rotation 54 of the bristle supporting structure 38, yet at a relative distance to said axis of rotation 54. Inserted in the bore 110 is a pin 112 whose free end which protrudes beyond the annular shoulder 61 extends through the eyelet 103 of the rod 102. The diameter of the eyelet 103 is slightly larger than the diameter of the pin 112, thus enabling the eyelet 103 to rotate about the pin 112 as well as to move to and fro in an axial direction of the pin 112.

As a result, the rod 102 and thus the shaft 34 of the brush section 24 are coupled to the pin 112 and thus to the bristle supporting structure 38 through the eyelet 103.

The mode of operation of the coupling in the turned-on condition of the electric toothbrush will now be explained with reference to FIGS. 2a to 2c. While FIG. 2a shows this coupling in the mid-position, FIGS. 2b and 2c show the two extreme positions.

Figure 2A:
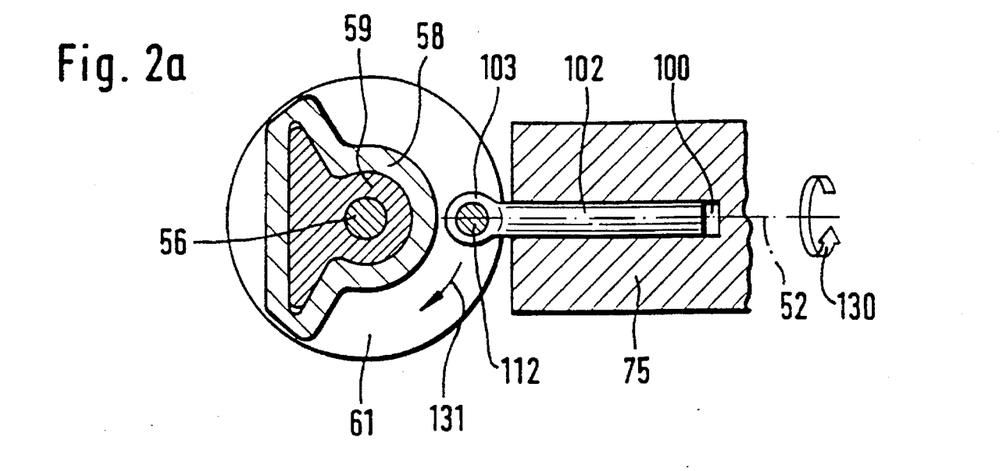
FIGS. 2a to 2c are schematic sectional views of the brush section taken along the line II—II of FIG. 1.

When the shaft 34 and thus the shaft member 75 are caused to rotate about the axis of rotation 52 in the direction indicated by the arrow 130, this results in a downward movement of the rod 102 when viewing FIG. 2a. Through the eyelet 103 and the pin 112, the annular shoulder 61 and thus the bristle supporting structure 38 are thereby caused to rotate about the axle 56 in the direction indicated by the arrow 131. As this rotary motion occurs, the rod 102 moves a length out of its bore 100 to compensate for the increasing distance of the pin 112 relative to the shaft member 75. At the same time, the eyelet 103 turns about the pin 112, equally in order to compensate for the rotation of the annular shoulder 61 about the axle 56. The rotary motions indicated by the arrows 130 and 131 will continue until the extreme position illustrated in FIG. 2b is attained.

Figure 2B:
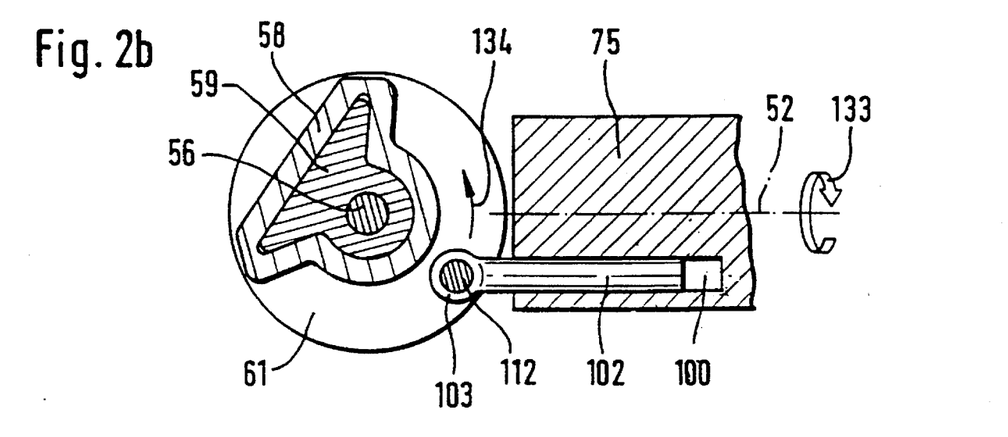

In the extreme position illustrated in FIG. 2b, the shaft member 75 reverses direction, rotating in the direction of arrow 133. This rotary motion of the shaft member 75 is transmitted through the rod 102, the eyelet 103, and the pin 112 to the annular shoulder 61 and thus to the bristle supporting structure 38 which will then rotate in the direction of the arrow 134. As this rotation occurs, first the relative distance of the pin 112 and the shaft member 75 is reduced, initially causing the rod 102 to engage within the bore 100 more deeply. However, as soon as the mid-position shown in FIG. 2a is exceeded, the rod 102 moves again out of the bore 100 as a result of a progressively increasing distance. Further, the eyelet 103 rotates about the pin 112 during all these rotary motions.

Figure 2C:
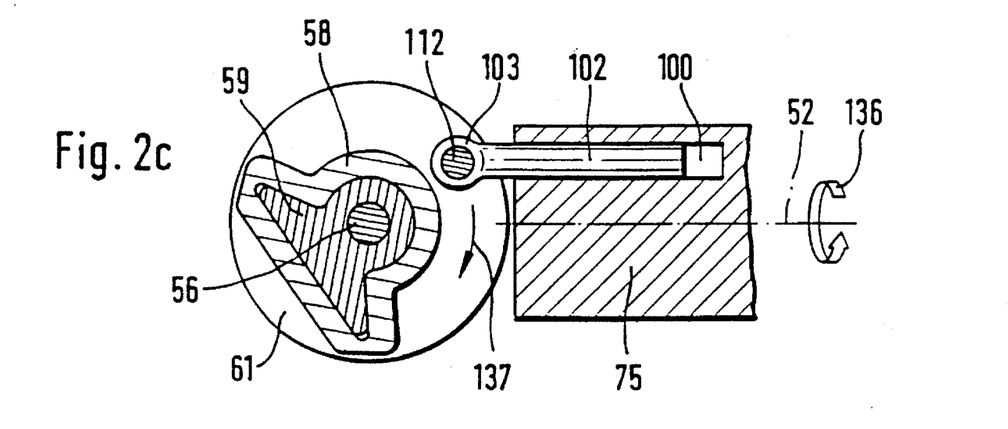

When the other extreme position illustrated in FIG. 2c is attained, the directions of rotation will reverse again, as shown in FIG. 2c by the arrows 136 and 137. The rod 102 moves again inside the bore 100, and the eyelet 103 rotates again about the pin 112. Then the midposition shown in FIG. 2a is reached, which completes a full cycle.

It will thus be seen that, overall, the alternating rotary motion of the shaft 34 transmitted through the rod 102, the eyelet 103, and the pin 112 causes the bristle supporting structure 38 to perform equally an alternating rotary motion.

The range of the angle of rotation traveled by the bristle supporting structure 38 is adjustable by selecting the relative distance of the bore 100 and the axis of rotation 52 of the shaft 34, as well as by selecting the relative distance of the bore 110 and the axis of rotation 54 of the bristle supporting structure 38. The preferred range of the angle of rotation of the bristle supporting structure 38 may be of the order of around +/−35°.

The second embodiment of a brush section 24 illustrated in FIG. 3 corresponds largely to the first embodiment described with reference to FIG. 1. Accordingly, essentially only those features that differ will be described in more detail in the following.

Figures 3, 4:
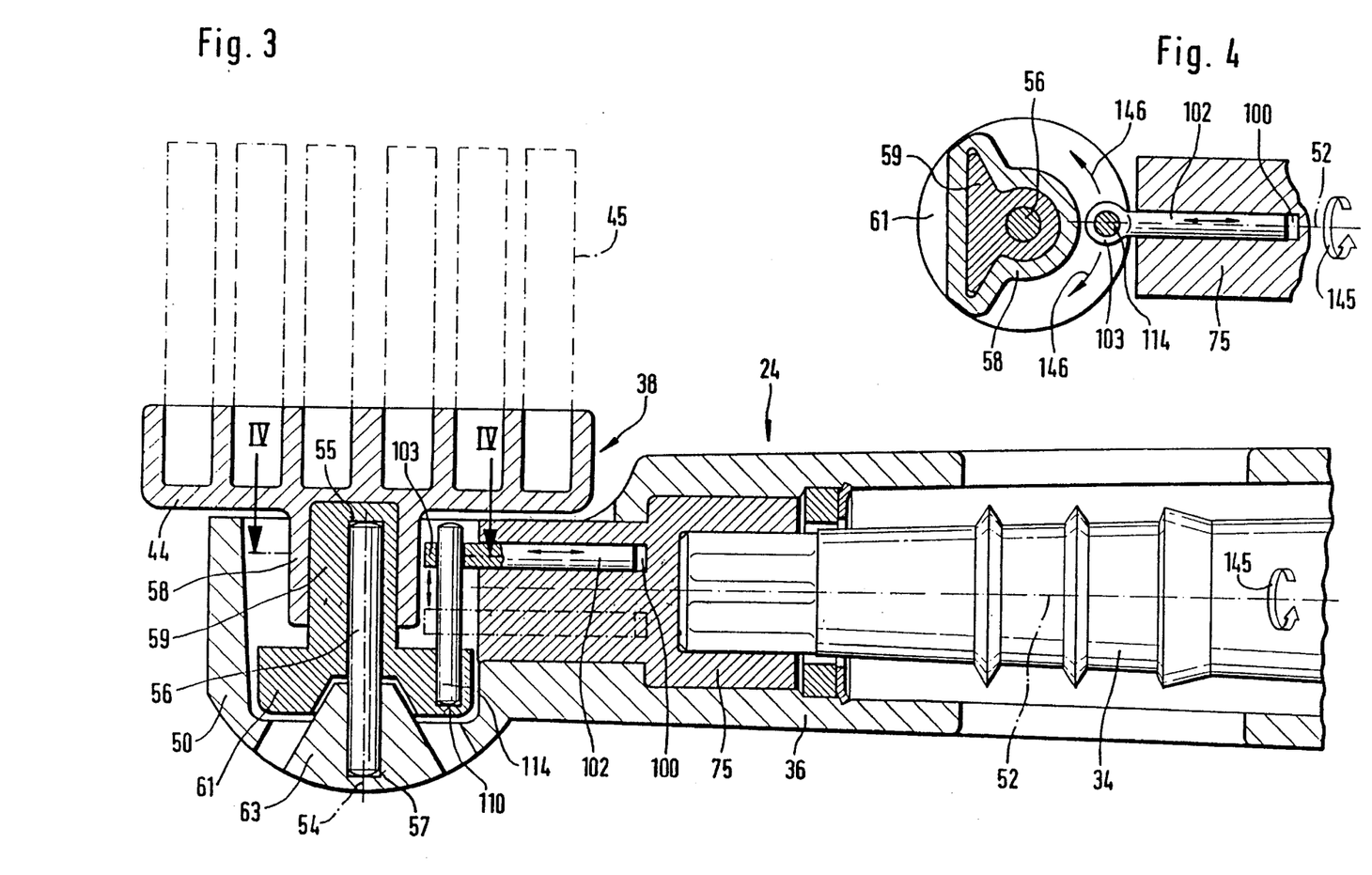
FIG. 3 is a schematic sectional view of a second embodiment of the brush section of an electric toothbrush constructed in accordance with the present invention, in which the shaft is driven to perform a rotary motion.
FIG. 4 is a schematic sectional view of the brush section taken along the line IV—IV of FIG. 3.

In the brush section of FIG. 3, the shaft 34 is caused to perform rotary motions. This is indicated by the arrow 145. The brush section 24 of FIG. 3 includes a pin 114 inserted in the bore 110 of the annular shoulder 61. As the pin 112 of FIG. 1, the pin 114 is arranged about parallel to the axis of rotation 54 of the bristle supporting structure 38, yet at a relative distance to said axis of rotation 54. The pin 114 of FIG. 3 is of a longer dimension that the pin 112 of FIG. 1.

The mode of operation of the coupling between the shaft 34 and the bristle supporting structure 38 as accomplished through the rod 102, the eyelet 103, and the pin 114 will be explained in more detail in the following with reference to FIG. 4.

When the shaft 34 and thus the shaft member 75 are caused to rotate about the axis of rotation 52 as indicated by the arrow 145 in FIG. 4, this results in the rod 102 being continuously moved up and down relative to the axis of rotation 52. The rod 102 being coupled to the pin 114 through the eyelet 103, this causes a rotary motion of the annular shoulder 61 and thus of the bristle supporting structure 38 about the axle 56. As a result of the up-and-down movement of the rod 102, the rotary motion of the annular shoulder 61 is a rotary motion reversing direction in alternating sequence, as indicated in FIG. 4 by the arrows 146.

As the shaft 34 rotates, the rod 102 moves axially back and forth inside the bore 100. Further, the eyelet 103 oscillates about the pin 114, in addition to moving up and down in an axial direction of the pin 114. Overall, it will be seen that the rotary motion of the shaft 34 transmitted through the rod 102, the eyelet 103, and the pin 114 is converted into an alternating rotary motion of the bristle supporting structure 38.

As already mentioned, also in this embodiment the range of the angle of rotation traveled by the bristle supporting structure 38 is adjustable by selecting the relative distances of the rod 102 or the pin 114 and the axes of rotation 52 and 54 of the shaft 34 and the bristle supporting structure 38, respectively. Again, an angle of rotation in the range of around +/−35° is preferred.

Figure 5:
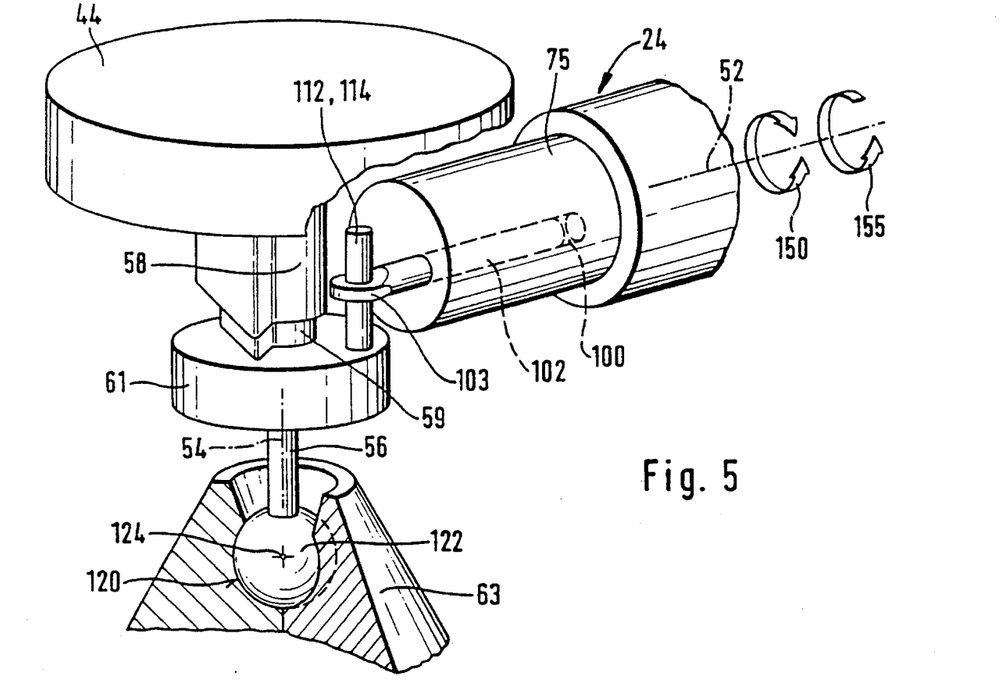
FIG. 5 is a schematic perspective view of a third embodiment of the brush section of an electric toothbrush constructed in accordance with the present invention.

The third embodiment of a brush section 24 illustrated in FIG. 5 corresponds in part to the first and second embodiment of FIGS. 1 to 4. Accordingly, only differing features will be set out in the following.

The shaft 34 and the shaft member 75 of the brush section 24 shown in FIG. 5 may be caused to perform rotary as well as alternating motions. This is shown in FIG. 5 by the arrows 150 and 155. When caused to perform alternating motions, a shorter pin 112 is used, whilst a rotary motion employs a longer pin 114.

In the third embodiment of FIG. 5, the essential difference of the brush section 24 of FIG. 5 is that the axle 56, rather than being received in the blind-end bore 57 as in the embodiments of FIGS. 1 to 4, is provided with a bearing ball 122 carried in a ball bearing 120. In this embodiment, the ball bearing 120 is mounted in the elevation 63 of the brush section 24, causing the axle 56 to be pivotal about a point 124.

Another difference is that the rod 102 is fixed inside its bore 100 in an axial direction. This means that the rod 102, while being allowed to rotate about its own axis within the bore 100, is immovable in its axial direction.

When the shaft 34 is caused to perform rotary or alternating motions, this results in an alternating rotary motion of the annular shoulder 61 and thus of the bristle supporting structure 38, as explained in the foregoing with reference to FIGS. 1 to 4. However, as the rod 102 is axially fixed within its bore 100, the continually changing distance of the pin 112 or 114 to the shaft member 75 cannot be compensated for. As a result, the annular shoulder 61 and thus the entire bristle supporting structure 38 are required to compensate for this changing distance. This is accomplished by means of the pivotal bearing of the axle 56, allowing the bristle supporting structure 38 to pivot about the point 124. Thus, the bristle supporting structure 38 executes on the whole an alternating rotary and wobbling motion.

Figure 6:
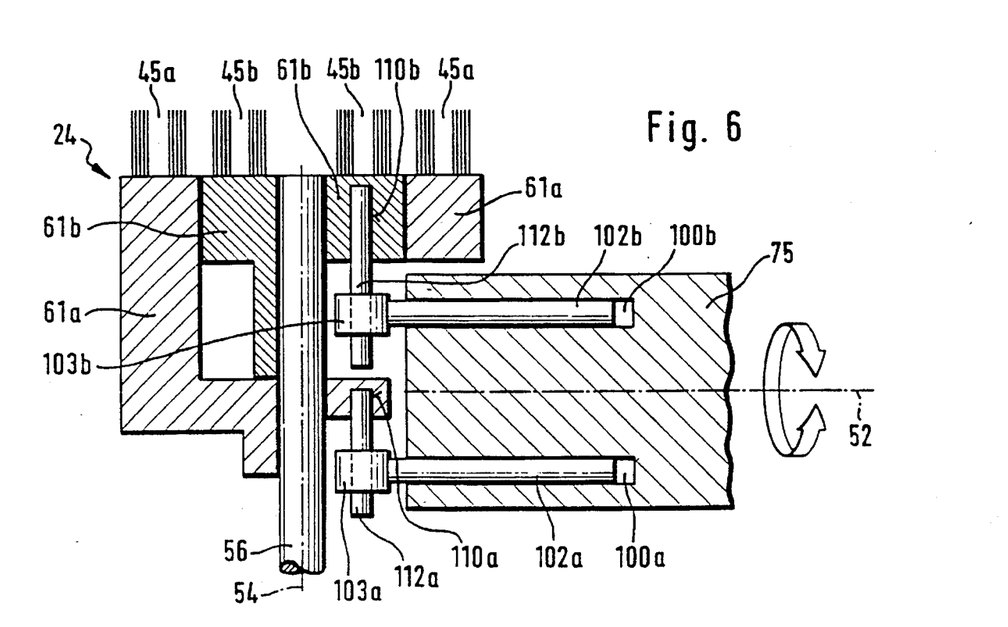
FIG. 6 is a schematic sectional view of a fourth embodiment of the brush section of an electric toothbrush constructed in accordance with the present invention.
Figure 7A:
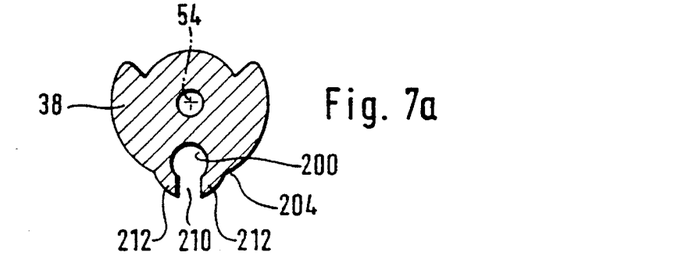
FIGS. 7a to 7e are a schematic side view and several sectional views of a fifth embodiment relating to the location of the transmission element on the bristle supporting structure.
Figure 7B:
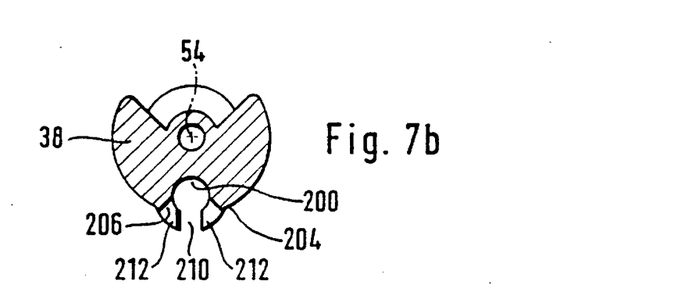
Figure 7C:
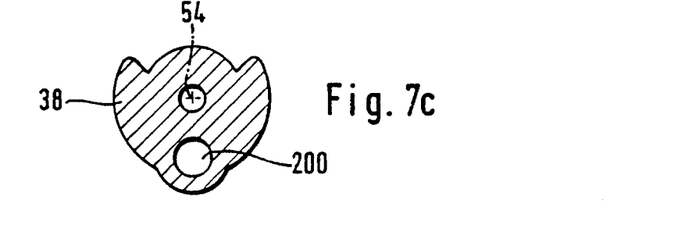
Figures 7D, 7E:
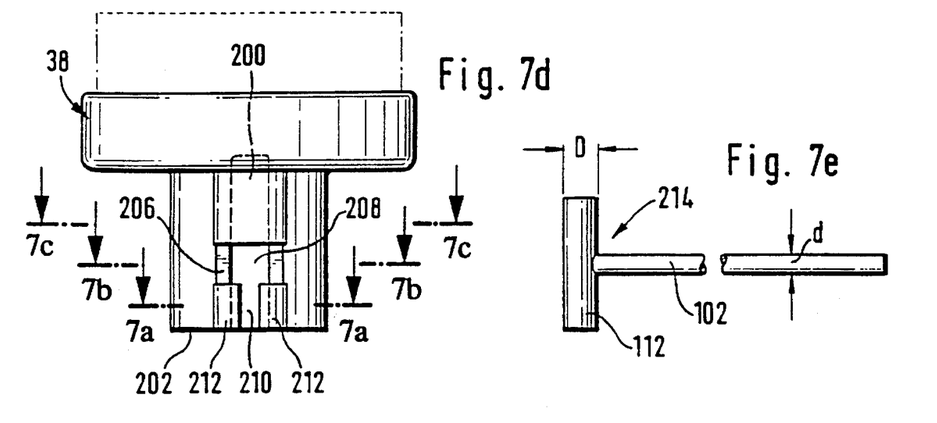
Figure 8A:
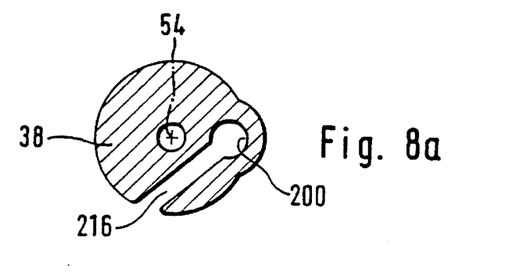
FIGS. 8a to 8e are a schematic side view and several sectional views of a sixth embodiment relating to the location of the transmission element on the bristle supporting structure.
Figure 8B:
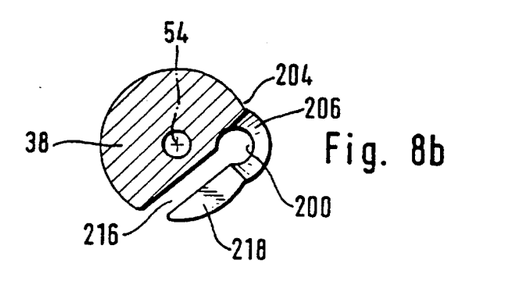
Figure 8C:
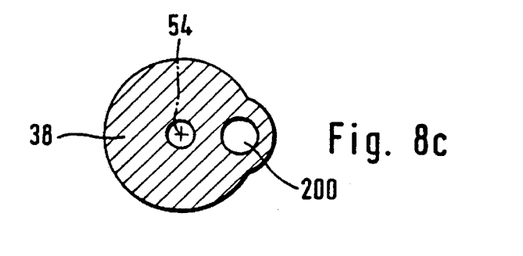
Figures 8D, 8E:
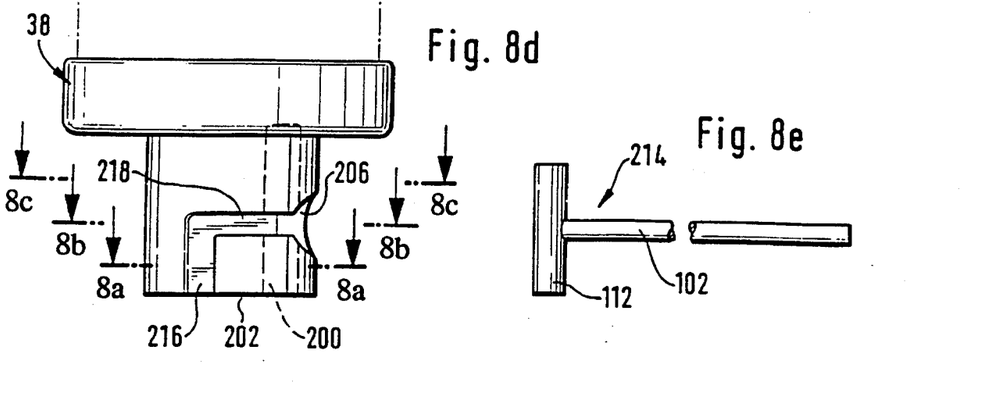

FIG. 6 shows a fourth embodiment in which a brush section 24 includes an outer and an inner ring of bristles. For reasons of simplicity, these two bristle rings are shown in FIG. 6 as an outer annular shoulder 61a and an inner annular shoulder 61b arranged concentrically with the axis of rotation 54. The outer annular shoulder 61a carries the bristles 45a, while the inner annular shoulder 61b carries the bristles 45b. It will be understood that in the embodiment of FIG. 6 the bristles 45a and 45b may also be held in plate or ring carriers which may then be connected to the annular shoulders 61a and 61b in the manner disclosed in the embodiments of FIGS. 1 to 5.

The shaft member 75 is provided with two bores 100a and 100b disposed parallel, yet at a distance and thus eccentric to, the axis of rotation 52, each bore receiving a respective rod 102a and 102b. The rods 102a and 102b are rotary as well as axially movable within their respective bores 100a and 100b. At the free ends of the rods 102a and 102b, a respective eyelet 103a and 103b is provided.

Formed in the outer annular shoulder 61a is a bore 110a in which a pin 112a is inserted. The pin 112a is disposed in parallel and eccentrically to the axis of rotation 54 of the axle 56 of the bristle supporting structure 38. Further, the pin 112a is passed through the eyelet 103a, the eyelet 103a being rotatable about the pin and movable to and fro in the axial direction of the pin.

Correspondingly, a bore 110b is formed in the annular shoulder 61b, with a pin 112b being inserted therein which further extends through the eyelet 103b.

As becomes apparent from FIG. 6, the bores 100a and 100b are arranged at opposite sides eccentrically to the axis of rotation 52 of the shaft 34. By coupling the rods 102a and 102b to the pins 112a and 112b through the eyelets 103a and 103b, the outer annular shoulder 61a and the inner annular shoulder 61b execute alternating rotary motions in opposite directions. Overall, in the embodiment of FIG. 6 an alternating rotary motion of the shaft 34 is converted into an alternating rotary motion in opposite direction of both bristle rings.

FIGS. 7a–7e show a fifth embodiment relating to the location of the transmission element 214 comprised of the rod 102 and the pin 112. Eccentrically disposed in the bristle supporting structure 38 is a bore 200 opening towards the underside 202 of the bristle supporting structure 38 and serving to receive the pin 112 which is integrally formed with the rod 102. The transmission element 214 is of a T-shaped configuration, the short beam being formed by pin 112 and the long beam by the rod 102. Advantageously, the rod 102 is of a smaller diameter than the pin 112. In a center portion of the bristle supporting structure 38, the bore 200 has an aperture 206 towards the side wall 204 of the bristle supporting structure, in which aperture the rod 102 is received so as to be slidable axially and pivotal laterally after the transmission element 214 is mounted on the bristle supporting structure 38. To mount the transmission element 214, a longitudinally slotted opening 208 extending radially to the side wall 204 and preferably including a narrowing 210 formed by extensions 212 is provided in a lower portion of the bore 200 of the bristle supporting structure 38. To mount the transmission element 214 on the bristle supporting structure 38, its pin 112 is introduced into the bore 200 and urged axially upwardly, while the rod 102 is received in the longitudinally slotted opening 208 as this assembly operation is performed. The narrowing 210 is such as to allow ready passage of the reduced-diameter rod 102, whilst however the lower portion of the pin 112 is fixedly located in the bore 200 by the extensions 212.

In FIGS. 8a–8e show, in a lower portion of the bore 200 of the bristle supporting structure 38 an essentially chord-like notch 216 is provided which is open towards the underside 202 and is in communication with a further notch 218 provided in the side wall 204. Again, the pin 112 of the transmission element is introduced into the bore 200, in which process the rod is swung away from the aperture 206 at a rearward inclination, enabling it to be received by the notch 216. The transmission element 214 is displaced axially upwardly in the direction of the axis of the bore 200, until the rod 102 engages within the notch 218. This then enables the transmission element 214 to be swung radially outwardly about the pin 112, so that the rod 102 is received in the aperture 206. Both end portions of the pin 112 are located in the bore 200, an additional securing function being provided by the transmission element 214 being held captive within the bore 200.

Figure 9:
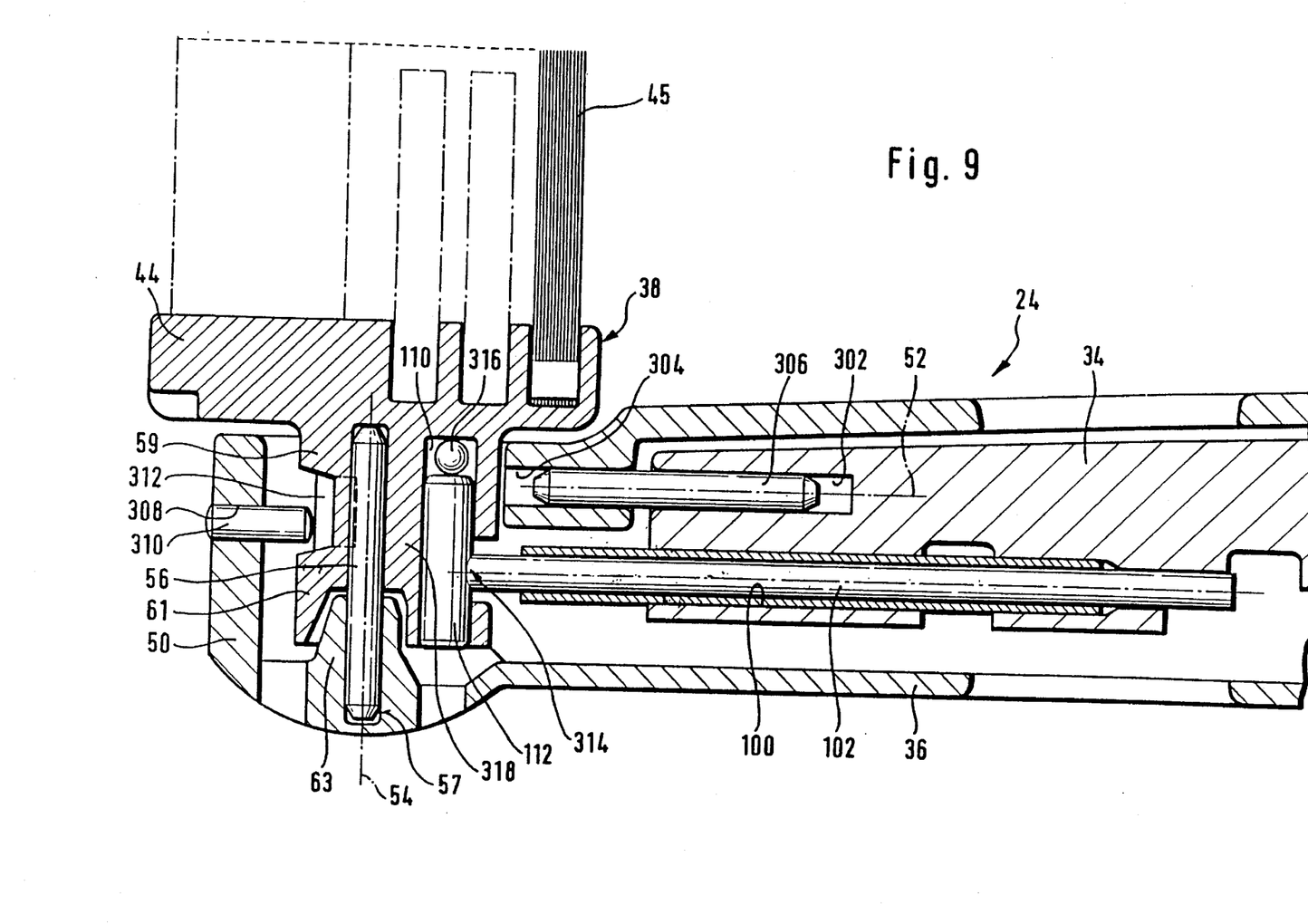
FIG. 9 is a schematic sectional view of a seventh embodiment of the brush section of an electric toothbrush constructed in accordance with the present invention, in which the bristle supporting structure is capable of executing a lifting motion in the direction of the axis of rotation, in addition to the oscillatory motion about the axis of rotation.

It is understood that the two embodiments of FIGS. 7a–7e and FIGS. 8a–8e may be combined in any desired way with the embodiments of FIGS. 1 to 6. FIG. 9 shows a further embodiment of this invention in which components identical to those in the preceding embodiments are assigned corresponding reference numerals. In the following, only the differences in construction and function will be described. The driving means and the driven means are integrally formed in the manner of a T-piece 314. The rod 102 is received in a mount, in particular a bore 100, arranged essentially parallel to the axis of rotation 52 of the shaft 34. The driving means is axially displaceable relative to the axis of rotation 52 of the shaft 34. Further, the shaft 34 includes a bore 302 concentric with the axis of rotation 52 and receiving an end of a pin 306. With its other end, the pin 306 engages in a bore 304 provided in the side wall of the cup-shaped socket 50. This arrangement ensures a reliable and clearance-free support of the shaft 34 in the mounting tube 36. The side wall of the cup-shaped socket 50 includes a further bore 308 receiving a pin 310. The pin 310 extends into the interior of the cup-shaped socket 50, engaging in a recess 312 of the trunnion 318 of the bristle supporting structure 38. By this means, the bristle supporting structure 38 is secured against axial displacement on the axle 56, or against slipping from said axle 56 inadvertently. In contrast to the preceding embodiments, the driven means configured in particular as the pin 112 inside the mount configured in particular as the bore 110 is fixedly coupled to the bristle supporting structure 38 in respect of an axial displacement in the direction of the axis of rotation 54. In particular, the possibility exists to restrict, or avoid altogether, an axial displacement of the driven means in the mount of the bristle supporting structure 38 by a limiting means 316 or similar locating means. As a result, the bristle supporting structure 38, in addition to performing an alternating oscillatory rotary motion about the axis of rotation 54, also executes a reciprocating lifting motion in the direction of the axis of rotation 54. Due to this fixed location of the driven means on the bristle supporting structure 38 in axial direction (related to the axis of rotation 54), the bristle supporting structure 38 is lifted a certain amount from the position illustrated in FIG. 9 in the direction of the axis of rotation 54, when the shaft 34 is rotated from the mid-position shown into either one of the two extreme positions to the left or right, related to the axis of rotation 52. Thus, the lifting stroke of the bristle supporting structure 38 is dependent on the eccentricity of the rod 102 or the height of the circular arc traveled by the rod 102 during a to-and-fro motion of the shaft 34. By virtue of the lifting stroke in the direction of the axis of rotation, which is superposed onto the oscillating rotary motion of the bristle supporting structure 38, the bristle ends, apart from executing a wiping motion, are also pressed against the teeth to be cleaned, thereby increasing the efficiency of tooth cleaning, not only in the interproximal spaces.

I claim:

1. A brush section for an electric toothbrush having
   a rotary shaft, said brush section receiving said rotary shaft when assembled onto the electric toothbrush and comprising:
   a rotary bristle supporting structure operatively coupled to the shaft and having an axis of rotation that is at about a right angle to an axis of rotation of the shaft, and
   a drive mechanism coupled to the shaft to drive the bristle supporting structure, said drive mechanism comprising
   a first driving member driven by the shaft and disposed eccentrically to the axis of rotation of the shaft, and
   a first driven member, operatively connected to said bristle supporting structure and disposed eccentrically to the axis of rotation of the bristle supporting structure, the first driving member and the first driven member being coupled to each other so as to prevent the driving member and the driven member from moving relative to each other in either direction that is parallel to the axis of the rotary shaft.

2. A brush section as claimed in claim 1, wherein the rotary shaft has a bore, arranged approximately parallel to the axis of rotation of the shaft and wherein the first driving member comprises a rod disposed in said bore.

3. A brush section as claimed in claim 1, wherein the rotary bristle supporting structure has a bore, arranged approximately parallel to the axis of rotation of the bristle supporting structure and wherein the first driven member comprises a pin disposed in said bore.

4. A brush section as claimed in claim 2, wherein the first driven member comprises a pin and wherein the rod has at a free end an eyelet through which the pin is passed, said rod being rotatable as well as axially movable inside the bore, said eyelet being rotatable about said pin as well as movable in the axial direction of the pin.

5. A brush section as claimed in claim 1 wherein the brush section further comprises an axle rotatable about the axis of rotation of the bristle supporting structure, said axle being pivotally mounted in the brush section and having the bristle supporting structure rotatably mounted thereon.

6. A brush section as claimed in claim 5, wherein the brush section further comprises
   a ball bearing,
   a bearing ball received in said ball bearing and connected to said axle.

7. A brush section as claimed in claim 2, wherein the rod is rotatably arranged in the bore of the shaft, while being non-displaceable in the axial direction along the bore of the shaft.

8. A brush section as claimed in claim 1, further comprising a second driving member and a second driven member coupled to said second driving member and wherein the bristle supporting structure includes an outer bristle ring and an inner bristle ring which are both rotatable about the axis of rotation of the bristle supporting structure, wherein the outer bristle ring is operatively associated with the first driven member and wherein the inner bristle ring is operatively associated with the second driven member.

9. A brush section as claimed in claim 8, wherein the first and the second driving members are disposed on relatively opposite sides of the axis of rotation of the shaft.

10. A brush section as claimed in claim 3, wherein the bore is eccentrically disposed in the bristle supporting structure and opens towards an underside of the bristle supporting structure, and wherein the first driven member and the first driving member are configured as an integral transmission element.

11. A brush section as claimed in claim 10, wherein the eccentrically disposed bore passes through a mid-section of the bristle supporting structure, the bore in the vicinity of said mid-section having an aperture extending towards a side wall of the bristle supporting structure.

12. A brush section as claimed in claim 10, wherein said first driving member comprises a rod having a diameter d, wherein said pin has a diameter D, wherein the transmission element formed by said pin and said rod is of a T-shaped configuration, and wherein the diameter d of the rod is smaller than the diameter D of the pin.

13. A brush section as claimed in claim 11, wherein a lower portion of the bore of the bristle supporting structure includes an opening which extends radially to the side wall in the manner of a longitudinal slot and includes a narrowing formed by extensions.

14. A brush section as claimed in claim 11, wherein a lower portion of the eccentrically disposed bore of the bristle supporting structure provides an essentially chord-like notch open towards the underside, said notch being in communication with a further notch provided in the side wall.

15. A brush section as claimed in claim 1 wherein the first driving member and the first driven member are integrally formed as a T-piece.

16. A brush section as claimed in claim 1, wherein the shaft includes a bore concentric with the axis of rotation of the shaft, said brush section further comprising a cup-shaped socket having a second bore in a side wall thereof, and a pin having one end disposed in the bore in the shaft and another end disposed in the second bore.

17. A brush section as claimed in claim 16, wherein the cup-shaped socket includes a third bore in its side wall, said bristle supporting structure includes a trunnion integrally formed therewith and having a recess, said brush section further comprising a pin having one end disposed in said third bore and another end disposed in said recess.

18. A brush section as claimed in claim 1, wherein the first driving member is axially displaceable with respect to the axis of rotation of the shaft.

19. A brush section as claimed in claim 1, wherein the bristle supporting structure includes a mount and the first driven member is held in the mount, is coupled thereto, and is axially displaceable along the axis of rotation of the bristle supporting structure.

20. A brush section as claimed in claim 19, wherein the brush section further comprises a limiting device that restricts displacement of the first driven member along the axis of rotation of the bristle supporting structure.

21. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, said bristle supporting structure having a bore, arranged approximately parallel to the axis of rotation of the bristle supporting structure, and a drive mechanism coupled to the shaft to drive the bristle supporting structure, said drive mechanism comprising a driving member driven by the shaft and disposed eccentrically to the axis of rotation of the shaft, and a pin operatively connected to and disposed within said bore of said bristle supporting structure and disposed eccentrically to the axis of rotation of the bristle supporting structure, the driving member and the pin being coupled to each other so as to prevent the driving member and the pin from moving relative to each other in either direction that is parallel to the axis of the rotary shaft.

22. A brush section for an electric toothbrush having a rotary shaft having a bore, arranged approximately parallel to the axis of rotation of the shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, and a drive mechanism coupled to the shaft to drive the bristle supporting structure, said drive mechanism comprising a rod driven by the shaft and disposed eccentrically to the axis of rotation of the shaft and within said bore of said shaft, said rod being rotatable as well as axially movable inside the bore, said rod having at a free end an eyelet, and a pin operatively connected to said bristle supporting structure and disposed eccentrically to the axis of rotation of the bristle supporting structure and through said eyelet, said eyelet being rotatable about said pin as well as movable in the axial direction of said pin so as to prevent the rod and the pin from moving relative to each other in either direction that is parallel to the axis of the rotary shaft.

23. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, an axle rotatable about the axis of rotation of the bristle supporting structure, said axle being pivotally mounted in the brush section and having the bristle supporting structure mounted thereon, and a drive mechanism coupled to the shaft to drive the bristle supporting structure, said drive mechanism comprising a driving member driven by the shaft and disposed eccentrically to the axis of rotation of the shaft, and a driven member operatively connected to said bristle supporting structure and disposed eccentrically to the axis of rotation of the bristle supporting structure, the driving member and the driven member being coupled to each other so as to prevent the driving member and the driven member from moving relative to each other in either direction that is parallel to the axis of the rotary shaft.

24. A brush section for an electric toothbrush having a rotary shaft having a bore, arranged approximately parallel to the axis of rotation of the shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, and a drive mechanism coupled to the shaft to drive the bristle supporting structure, said drive mechanism comprising a rod driven by the shaft and disposed eccentrically to the axis of rotation of the shaft and rotatably arranged in the bore of the shaft, while being non-displaceable in the axial direction along the bore of the shaft, and a driven member operatively connected to said bristle supporting structure and disposed eccentrically to the axis of rotation of the bristle supporting structure, the rod and the driven member being coupled to each other so as to prevent the rod and the driven member from moving relative to each other in either direction that is parallel to the axis of the rotary shaft.

25. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, and a drive mechanism coupled to the shaft to drive the bristle supporting structure, said drive mechanism comprising a first driving member driven by the shaft and disposed eccentrically to the axis of rotation of the shaft, a first driven member in contact with said bristle supporting structure and disposed eccentrically to the axis of rotation of the bristle supporting structure, the first driving member and the first driven member being coupled to each other so as to prevent the driving member and the driven member from moving relative to each other in either direction that is parallel to the axis of the rotary shaft, and a second driving member and a second driven member coupled to said second driving member and wherein the bristle supporting structure includes an outer bristle ring and an inner bristle ring which are both rotatable about the axis of rotation of the bristle supporting structure, wherein the outer bristle ring is operatively associated with the first driven member and wherein the inner bristle ring is operatively associated with the second driven member.

26. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, said bristle supporting structure having a bore, arranged approximately parallel to the axis of rotation of the bristle supporting structure, the bore being eccentrically disposed in the bristle supporting structure and opening toward an underside of the bristle supporting structure, and a drive mechanism coupled to the shaft to drive the bristle supporting structure, said drive mechanism comprising a driving member driven by the shaft and disposed eccentrically to the axis of rotation of the shaft, and a pin disposed within said bore of said bristle supporting structure, the driving member and the pin configured as an integral transmission element so as to prevent the driving member and the pin from moving relative to each other in either direction that is parallel to the axis of the rotary shaft.

27. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, said bristle supporting structure having a bore, arranged approximately parallel to the axis of rotation of the bristle supporting structure, and a drive mechanism connected to the shaft to drive the bristle supporting structure, said drive mechanism comprising a driving member operatively connected to the shaft and disposed eccentrically to the axis of rotation of the shaft, and a driven member in contact with said bristle supporting structure and disposed eccentrically to the axis of rotation of the bristle supporting structure, the driven member and the driving member configured as an integral transmission element so as to prevent the driving member and the driven member from moving relative to each other in either direction that is parallel to the axis of the rotary shaft.

28. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, said bristle supporting structure having a bore, arranged approximately parallel to the axis of rotation of the bristle supporting structure, the bore being eccentrically disposed in the bristle supporting structure and opening toward an underside of the bristle supporting structure, and a drive mechanism coupled to the shaft to drive the bristle supporting structure, said drive mechanism comprising a rod driven by the shaft and disposed eccentrically to the axis of rotation of the shaft, wherein said rod has a diameter d, and a pin, operatively connected to said bristle supporting structure, having a diameter D, wherein the rod and the pin are configured as an integral transmission element of a T-shaped configuration, and wherein the diameter d of the rod is smaller than the diameter D of the pin so as to prevent the pin and the rod from moving relative to each other in either direction that is parallel to the axis of the rotary shaft.

29. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, and a drive mechanism coupled to the shaft to drive the bristle supporting structure, said drive mechanism comprising a driving member driven by the shaft and disposed eccentrically to the axis of rotation of the shaft, a driven member operatively connected to said bristle supporting structure and disposed eccentrically to the axis of rotation of the bristle supporting structure, the driving member and the driven member integrally formed as a T-piece so as to prevent the driving member and the driven member from moving relative to each other in either direction that is parallel to the axis of the rotary shaft.

30. A brush section for an electric toothbrush having a rotary shaft having a bore concentric with the axis of rotation of the shaft, said brush section receiving said rotary shaft when assembled onto the electric toothbrush and comprising:

a cup-shaped socket having a second bore in a side wall thereof,     a pin having one end disposed in the bore in the shaft and another end disposed in the second bore,     a rotary bristle supporting structure operatively coupled to the shaft and having an axis of rotation that is at about a right angle to an axis of rotation of the shaft, and     a drive mechanism coupled to the shaft to drive the bristle supporting structure, said drive mechanism comprising         a driving member driven by the shaft and disposed eccentrically to the axis of rotation of the shaft, and         a driven member operatively connected to said bristle supporting structure and disposed eccentrically to the axis of rotation of the bristle supporting structure, the driving member and the driven member being coupled to each other so as to prevent the driving member and the driven member from moving relative to each other in either direction that is parallel to the axis of the rotary shaft.

31. A brush section for an electric toothbrush having a rotary shaft, said brush section receiving said rotary shaft when assembled onto the electric toothbrush and comprising:

a rotary bristle supporting structure operatively coupled to the shaft and having an axis of rotation that is at about a right angle to an axis of rotation of the shaft, and     a drive mechanism coupled to the shaft to drive the bristle supporting structure, said drive mechanism comprising         a driving member driven by the shaft, disposed eccentrically to the axis of rotation of the shaft, and axially displaceable along the axis of rotation of the shaft, and         a driven member operatively connected to said bristle supporting structure and disposed eccentrically to the axis of rotation of the bristle supporting structure, the driving member and the driven member being coupled to each other so as to prevent the driving member and the driven member from moving relative to each other in either direction that is parallel to the axis of the rotary shaft.

32. A brush section for an electric toothbrush having a rotary shaft, said brush section receiving said rotary shaft when assembled onto the electric toothbrush and comprising:

a rotary bristle supporting structure operatively coupled to the shaft, said rotary bristle supporting structure having a mount and an axis of rotation that is at about a right angle to an axis of rotation of the shaft, and     a drive mechanism coupled to the shaft to drive the bristle supporting structure, said drive mechanism comprising         a driving member driven by the shaft and disposed eccentrically to the axis of rotation of the shaft, and         a driven member held in the mount of said bristle supporting structure, disposed eccentrically to the axis of rotation of the bristle supporting structure, and coupled thereto in respect of an axial displacement in the direction of the axis of rotation of the bristle supporting structure, the driving member and the driven member being coupled to each other so as to prevent the driving member and the driven member from moving relative to each other in either direction that is parallel to the axis of the rotary shaft.

33. An electric toothbrush comprising:

a handle section including a rotary shaft and a motor which drives said rotary shaft;

a brush section which assembles onto said handle section and receives said rotary shaft, said brush section comprising:

a rotary bristle supporting structure operatively coupled to the shaft and having an axis of rotation that is at about a right angle to an axis of rotation of the shaft, and         a drive mechanism coupled to the shaft to drive the bristle supporting structure, said drive mechanism comprising:

a first driving member driven by the shaft and disposed eccentrically to the axis of rotation of the shaft, and             a first driven member operatively connected to said bristle supporting structure and disposed eccentrically to the axis of rotation of the bristle supporting structure, the first driving member and the first driven member being coupled to each other so as to prevent the first driving member and the first driven member from moving relative to each other in either direction that is parallel to the axis of the rotary shaft.

34. An electric toothbrush as claimed in claim 33, wherein the rotary shaft is adapted to be driven so as to perform both an alternating and a rotary motion.

35. An electric toothbrush as claimed in claim 33, wherein the rotary shaft has a bore, arranged approximately parallel to the axis of rotation of the shaft and wherein the first driving member comprises a rod disposed in said bore.

36. An electric toothbrush as claimed in claim 33, wherein the rotary bristle supporting structure has a bore, arranged approximately parallel to the axis of rotation of the bristle supporting structure and wherein the first driven member comprises a pin disposed in said bore.

37. An electric toothbrush as claimed in claim 35, wherein the first driven member comprises a pin and wherein the rod has at a free end an eyelet through which the pin is passed, said rod being rotatable as well as axially movable inside the bore, said eyelet being rotatable about said pin as well as movable in the axial direction of the pin.

38. An electric toothbrush as claimed in claim 33 wherein the brush section further comprises an axle rotatable about the axis of rotation of the bristle supporting structure, said axle being pivotally mounted in the brush section and having the bristle supporting structure rotatably mounted thereon.

39. An electric toothbrush as claimed in claim 33, further comprising a second driving member and a second driven member coupled to said second driving member and wherein the bristle supporting structure includes an outer bristle ring and an inner bristle ring which are both rotatable about the axis of rotation of the bristle supporting structure, wherein the outer bristle ring is operatively associated with the first driven member and wherein the inner bristle ring is operatively associated with the second driven member.

\* \* \* \* \*

UNITED STATES PATENT AND TRADEMARK OFFICE
CERTIFICATE OF CORRECTION

PATENT NO. : 5,577,285
DATED : November 26, 1996
INVENTOR(S) : Michael Drossler

It is certified that error appears in the above-identified patent and that said Letters Patent is hereby corrected as shown below:

Title page, item [56], under References Cited insert--
Systematik der Getriebe, pp. 34-37--.

Signed and Sealed this

Twelfth Day of January, 1999

Attest:

Attesting Officer

*Acting Commissioner of Patents and Trademarks*